United States Patent [19]
Dudley et al.

[11] Patent Number: 5,696,356
[45] Date of Patent: Dec. 9, 1997

[54] PASSIVE SOUND GATHERING APPARATUS

[75] Inventors: James P. Dudley, Sacramento; Kyle D. Fields, El Dorado Hills; Timothy J. Landis, Loomis, all of Calif.

[73] Assignee: Op-D-Op, Inc., Roseville, Calif.

[21] Appl. No.: 612,165

[22] Filed: Mar. 7, 1996

[51] Int. Cl.⁶ ............... H04R 25/00; A42B 1/08
[52] U.S. Cl. ............... 181/136; 181/129; 2/423; 2/425
[58] Field of Search ............... 181/129, 130, 181/133, 136; 2/209, 423, 425; 381/156, 160

[56] References Cited

U.S. PATENT DOCUMENTS

| | | |
|---|---|---|
| 373,835 | 5/1887 | Pitre . |
| 1,761,666 | 6/1930 | Hinternesch ............... 181/136 |
| 1,856,324 | 5/1932 | Fensky ............... 181/129 |
| 2,810,445 | 10/1957 | Garrido ............... 181/129 |
| 3,938,616 | 2/1976 | Brownfield ............... 181/136 |
| 5,044,014 | 9/1991 | Cornale et al. . |
| 5,086,789 | 2/1992 | Tichy . |
| 5,231,704 | 8/1993 | Hildenbrand . |
| 5,361,419 | 11/1994 | Bernstein ............... 2/209 X |

FOREIGN PATENT DOCUMENTS

| | | |
|---|---|---|
| 912921 | 4/1954 | Germany . |
| 479645 | 4/1943 | Italy . |
| 586868 | 12/1958 | Italy . |
| 356552 | 9/1931 | United Kingdom . |

*Primary Examiner*—Khanh Dang
*Attorney, Agent, or Firm*—John P. O'Banion

[57] ABSTRACT

A head worn sound gathering apparatus having a pair of sound gathering horns with rearward facing apertures. Each sound gathering horn includes a tapered sound channeling tube portion which communicates with an ear covering. Sound received through the rearward facing apertures is amplified and directed to the ear coverings wherein the sounds reach the ears of a wearer. The sound gathering horns and ear covers are preferably worn in association with a helmet such as a cyclist helmet.

8 Claims, 8 Drawing Sheets

PASSIVE SOUND GATHERING APPARATUS

BACKGROUND OF THE INVENTION

1. Field of the Invention

This invention pertains to devices and methods for directional sound amplification, and more particularly to a head-worn, rearwardly disposed sound gathering apparatus for use by cyclists and the like which provides for passive amplification of sound from behind the wearer and which directs the amplified sound to the wearer's ears.

2. Description of the Related Art

The use of bicycles for exercise, commuting, vacations, and travel generally has steadily increased in recent years, and the number of bicycles and bicyclists have proliferated. Increasing health consciousness and environmental awareness are among the primary factors which have spurred the increase in bicycle use. An important problem associated with bicycle travel is that the hearing of cyclists, especially in the rearward direction, is reduced by the noise caused by air or wind rushing past the ears due to the speed of travel. The reduced hearing associated with bicycle travel increases the risk of collisions with motor vehicles or other bicycles, particularly vehicles approaching from the rear.

A variety of ear covering, ear protector, and wind-deflector devices have been developed to both protect the ears of cyclists and to reduce the wind noise associated with bicycle travel. Most of these devices comprise shell-shaped coverings which are held over the ears of a wearer by a resilient band or head encircling strap. Some of the previously disclosed ear covering apparatus include rearwardly disposed openings for allowing the wearer to receive sounds from the rear. However, none of the previously disclosed ear covering and ear protecting devices provide adequate rearward sound amplification which overcomes the wind noise associated with cycle travel sufficiently to allow cyclists to hear motor vehicles or other cyclists approaching from the rear.

Accordingly, there is a need for a sound gathering apparatus that provides for passive amplification of sounds from behind a wearer, which directs the amplified sound to a wearer's ears, and which overcomes the wind noise associated with bicycle travel. The present invention satisfies these need, as well as others, and generally overcomes the deficiencies found in prior devices.

SUMMARY OF THE INVENTION

The present invention pertains to a head-worn passive sound amplification apparatus for cyclists and the like which eliminates the wind noise associated with bicycle travel while passively directing or introducing sounds from behind the wearer to the wearer's ears. In general terms, the invention comprises one or more sound gathering horns for collecting, passively amplifying, and directing sound to the ears of a wearer, ear covers to eliminate wind noise, and means for coupling or attaching the sound gathering horns and ear covers to a wearer's head.

By way of example and not of limitation, the invention preferably utilizes a pair of sound gathering horns having apertures facing in a substantially rearward direction. The shape and orientation of the apertures on the horns may be varied to achieve particular sound gathering objectives. The sound gathering horns channel sounds to the wearer's ears, and may be curved or convoluted in shape to direct or introduce sound to the wearer's ears, but are preferably tapered in shape to provide for amplification of sounds. The ear covers preferably are aerodynamically shaped to provide for elimination of the ambient wind noise associated with bicycle travel. Rearward facing openings are included in the ear covers to provide cooling to the wearer's ears as well as to provide additional passive sound gathering. The means for coupling or attaching the sound gathering horns and ear covers to the wearer's head preferably comprises a cyclist helmet, with the sound gathering horns suitably positioned on the exterior of the helmet such that the apertures face generally in a rearward orientation. The sound gathering horns may be integral portions of the cyclist helmet and molded from the same material as the exterior shell of the helmet, or alternatively may be detachable and interchangeable between different cyclist helmets. The ear covers may likewise be integral to the cyclist helmet or detachable and interchangeable.

An object of the invention is to provide a sound gathering apparatus which passively introduces the sounds of traffic approaching from the rear to the ears of a cyclist.

Another object of the invention is to provide a sound gathering apparatus which eliminates the wind noise associated with bicycle travel.

Another object of the invention is to provide a sound gathering apparatus which does not require electronic amplification.

Another object of the invention is to provide a sound gathering apparatus which is aesthetically pleasant.

Another object of the invention is to provide a sound gathering apparatus which is easy to use.

Another object of the invention is to provide a sound gathering apparatus which increases or enhances the safety of bicycle travel and reduces the risk of collision or accidents.

Further objects of the invention will be brought out in the following portions of the specification, wherein the detailed description is for the purpose of fully disclosing the invention without placing limits thereon.

BRIEF DESCRIPTION OF THE DRAWINGS

The invention will be more fully understood by reference to the following drawings which are for illustrative purposes only.

DETAILED DESCRIPTION OF THE PREFERRED EMBODIMENT

Figure 1:
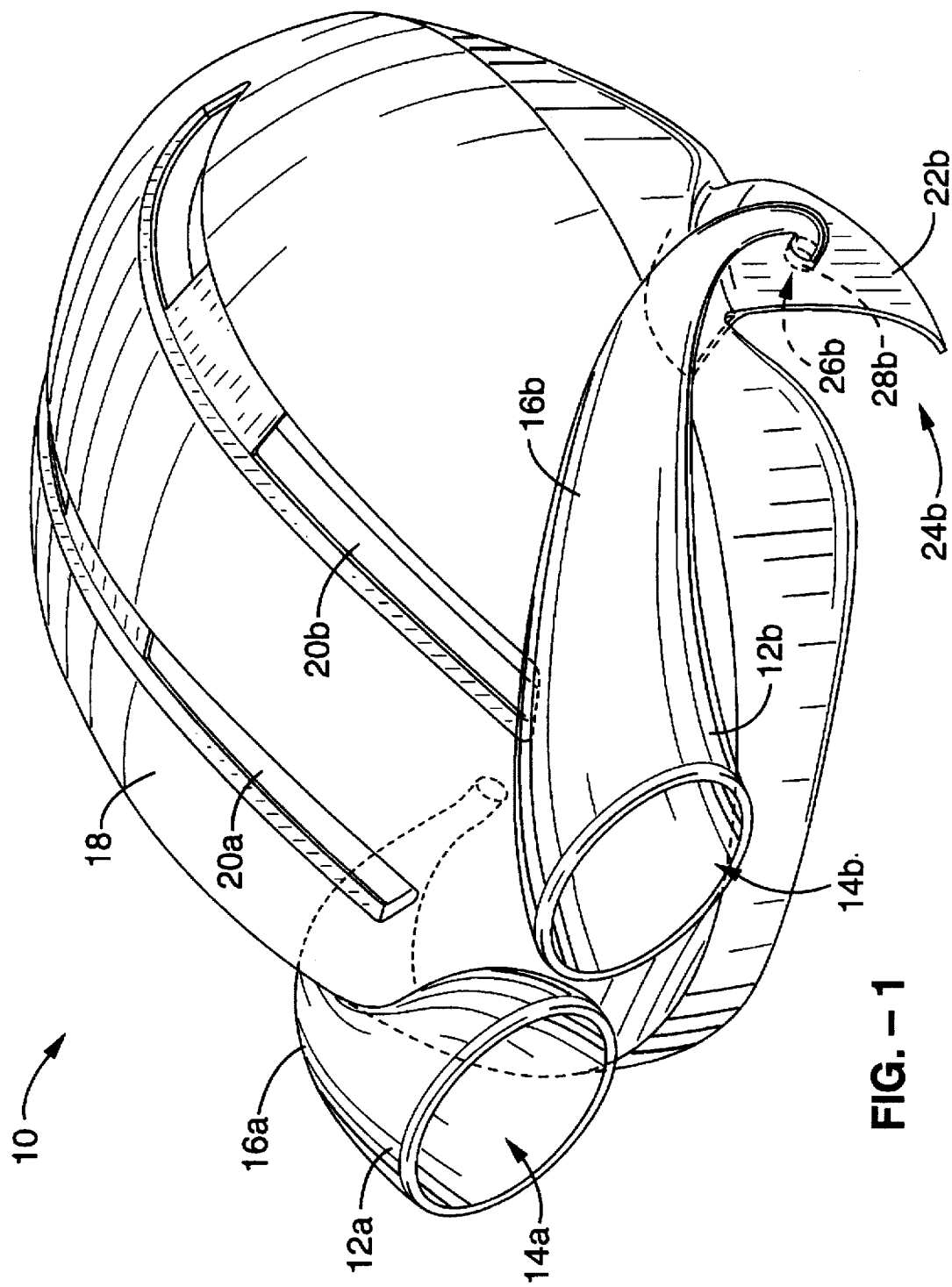
FIG. 1 is a perspective view of a first embodiment of a sound gathering apparatus in accordance with the invention.
Figure 2:
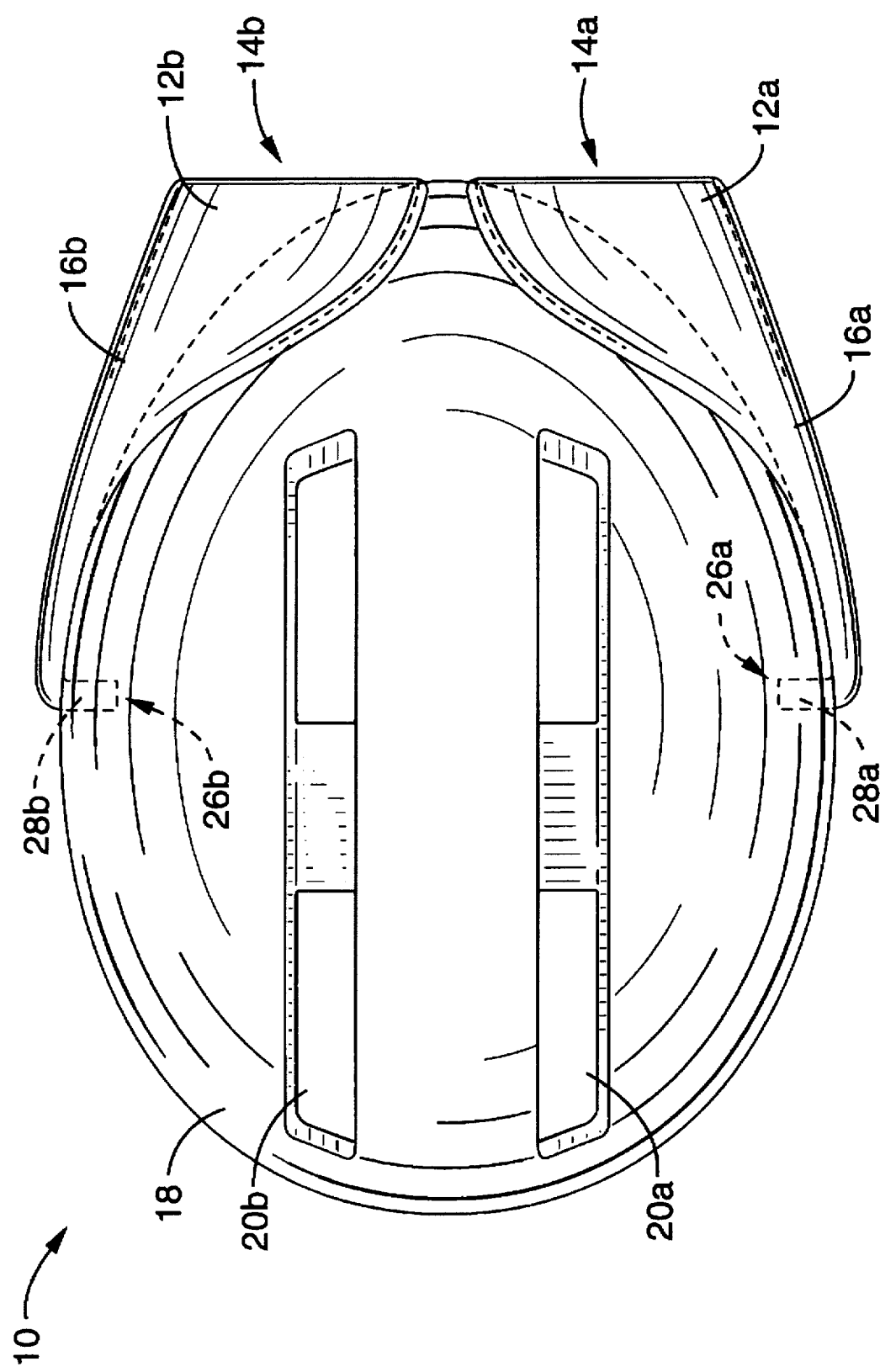
FIG. 2 is a top plan view of the sound gathering apparatus of FIG. 1.
Figure 3:
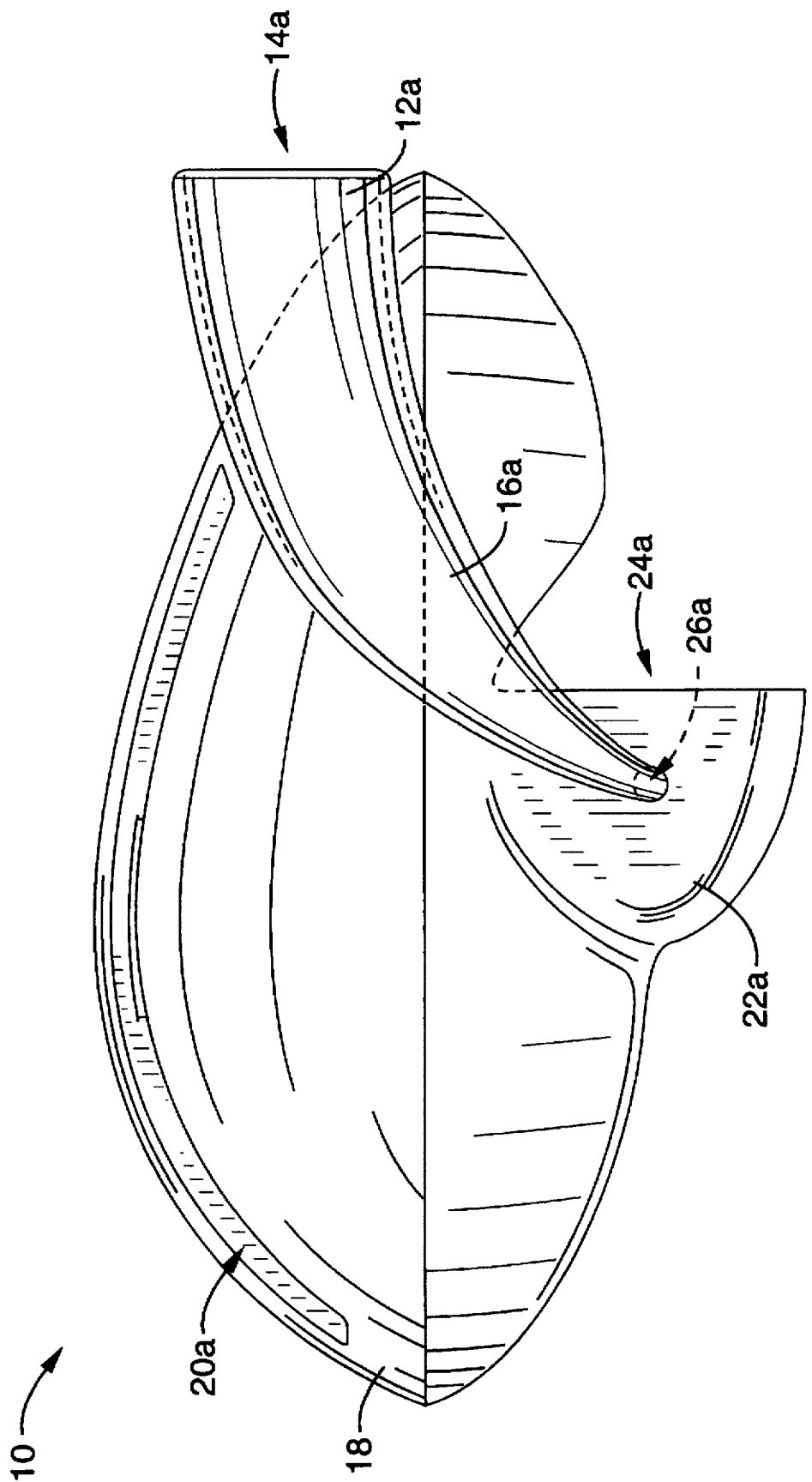
FIG. 3 is a side elevation view of the sound gathering apparatus of FIG. 1.
Figure 4:
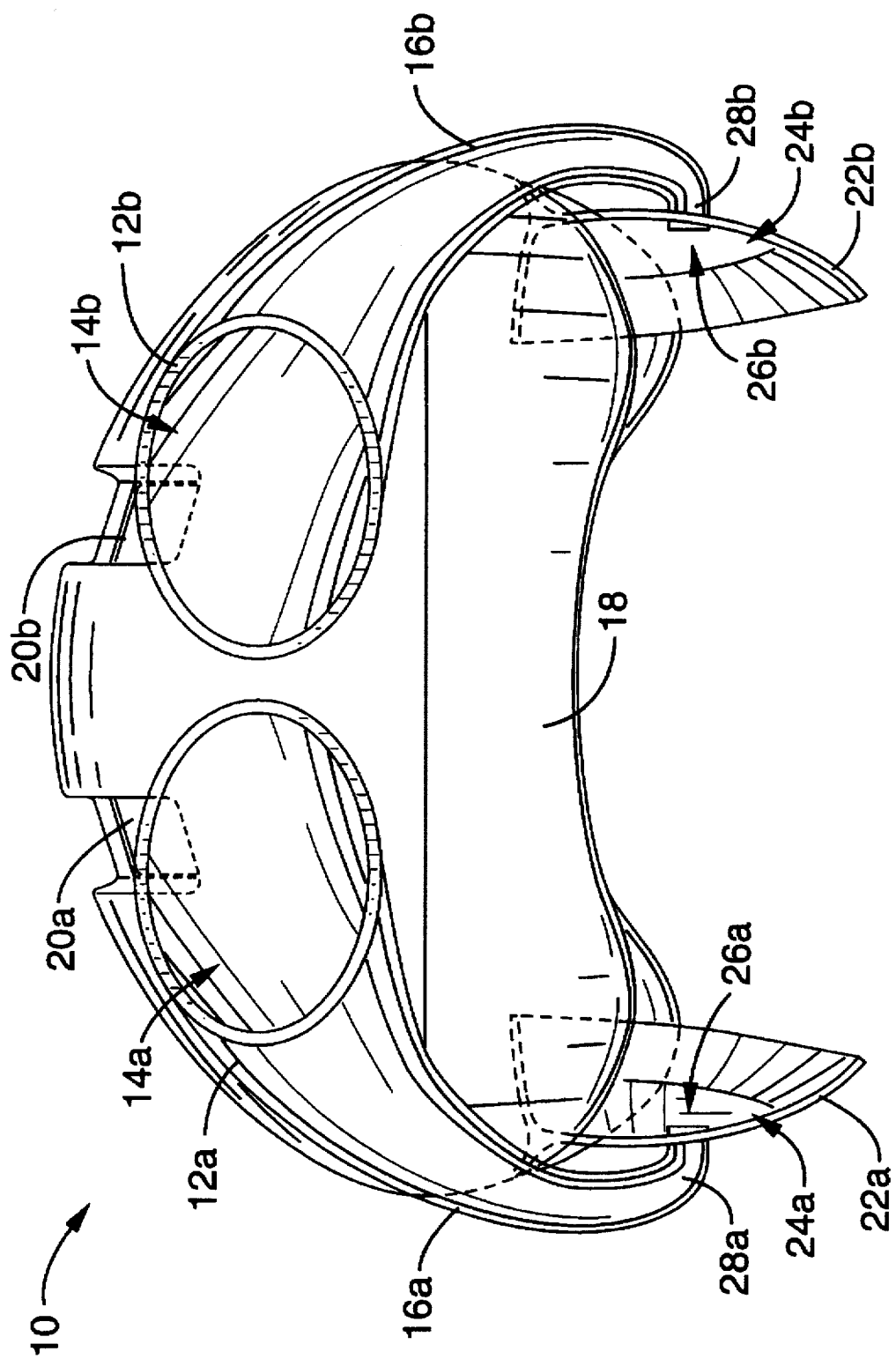
FIG. 4 is a rear view of the sound gathering apparatus of FIG. 1.

Referring more specifically to the drawings, for illustrative purposes the present invention is embodied in the apparatus which is generally shown in FIG. 1 through FIG. 8. It will be appreciated that the apparatus may vary as to configuration and as to details without departing from the basic concepts as disclosed herein. While the invention is disclosed in terms of use by bicyclists, it should be understood that the invention may also be utilized by motorcyclists and cyclists generally, as well as by persons involved in sports or other activities wherein directional sound enhancement may be advantageous.

Referring first to FIG. 1 through FIG. 4, there is shown a first embodiment of a head worn sound gathering apparatus 10 in accordance with the present invention which provides for gathering or receiving sound from behind a person wearing the invention and directing or introducing the sound to a wearer's ears. The invention generally includes first and second sound gathering horns 12a, 12b. Sound gathering horns 12a, 12b each include an aperture 14a, 14b respectively, with apertures 14a, 14b facing in a substantially rearward orientation. A variety of structures and configurations for sound gathering horns 12a, 12b and apertures 14a, 14b are contemplated for use with the invention, as will be readily apparent to persons of ordinary skill in the art. Sound gathering horns 12a, 12b may be positioned or structured and configured such that apertures 14a, 14b are oriented in any desired direction. However, it is presently contemplated that the invention will primarily be used for gathering or receiving sound from behind the wearer of the invention. Sound gathering horns 12a, 12b alternatively may each have a plurality of apertures.

Generally, first sound gathering horn 12a includes a sound channelling tube portion 16a which communicates with aperture 14a. Likewise, second sound gathering horn 12b includes a sound channelling tube portion 16b which communicates with aperture 14b. Sound channelling tubes 16a, 16b introduce amplified sound received by apertures 14a, 14b to a wearer's ears, as discussed further below. While sound channelling tubes 16a, 16b are shown as slightly curved in shape, the use of convoluted or turbinate shaped sound gathering tubes with the invention is also contemplated. However, sound channelling tubes 16a, 16b should preferably be curved or tapered in shape as shown to provide for amplification of sound received at apertures 14a, 14b. Sound gathering horns 12a, 12b preferably are fabricated from a durable, high strength polymeric material such as an engineering resin.

Means for coupling or attaching sound gathering horns 12a, 12b are provided with the invention. In the preferred embodiments, the coupling means comprises a cyclist helmet 18 which is worn by the user of the invention in a conventional fashion. Helmet 18 generally includes an interior, shock-absorbing foam core and an exterior, hard, impact-resistant shell as are standard in the art. A pair of longitudinal ventilation apertures or slots 20a, 20b are also included on helmet to increase wearer comfort. Sound gathering horns 12a, 12b are preferably affixed or attached to helmet 18 such that sound gathering horns 12a, 12b are symmetrically positioned on each side of helmet 18 in an opposing relationship as shown, with apertures 14a, 14b facing in a substantially rearward facing direction or orientation. Sound gathering horns 12a, 12b may be integral portions of helmet 18 and molded from the same material as the exterior shell of helmet 18, or may be separate pieces which are permanently affixed to helmet 18 by adhesives, melt bonding, or the like. Alternatively, sound gathering horns 12a, 12b may be separate pieces which are detachable and interchangeable between different helmets by standard means such as snap fitting or VELCRO® type hook and loop fasteners. It is also possible for sound gathering horns 12a, 12b to be adjustably attached onto helmet 18 to provide selective directional sound gathering. In the presently preferred embodiments of the invention, sound gathering horns 12a, 12b are integral to helmet 18 and are molded from the same impact resistant polymeric material as the exterior shell of helmet 18.

The means for coupling sound gathering horns 12a, 12b to a wearer's head may alternatively comprise a head encircling band, with sound gathering horns 12a, 12b coupled to the head band and held thereby onto a wearer's head in generally the same position and orientation as shown generally in FIG. 1 through FIG. 4. The use of eyeglass or goggle frames and hats as means for supporting sound gathering horns 12a, 12b are also contemplated.

A pair of ear covers or housings 22a, 22b are also generally provided with sound gathering apparatus 10, to eliminate the wind noise inherent in bicycle travel and further provide for direction of amplified sound to the wearer's ears. Ear covers 22a, 22b are preferably integral portions of helmet 18 as shown, with helmet 18 thus serving as means for attaching ear covers 22a, 22b to a wearer's head. Ear covers 22a, 22b may alternatively be detachable and interchangeable pieces which may be utilized with different helmets with reversible coupling means such as snap fitting or VELCRO® type hook and loop fasteners. Preferably, rearward facing apertures 24a, 24b are provided with ear covers 22a, 22b respectively. Apertures 24a, 24b serve to provide cooling to the wearer's ears and to provide additional passive sound amplification from the rear. Ear covers 22a, 22b are preferably structured and configured to provide an aerodynamic exterior shape to minimize wind noise adjacent to the ears of the wearer. Acoustic and/or thermal insulation (not shown) may be provided within ear covers 22a, 22b to further reduce background noise. Note that the invention may be utilized without ear covers 22a, 22b. However, due to the ambient wind noise associated with air flowing past the ears of cyclists, it is preferable to employ ear coverings 22a, 22b.

First and second sound channelling tubes 16a, 16b communicate with ear covers 22a, 22b by apertures 26a, 26b on ends 28a, 28b of sound channelling tubes 16a, 16b respectively. The apertures 26a, 26b in ends 28a, 28b serve to introduce sound received and amplified by sound gathering horns 12a, 12b to the ears of the wearer. Soft, resilient tubes (not shown) may be fastened onto ends 28a, 28b and inserted into the wearer's ears to provide further sound direction and amplification.

The sound gathering apparatus 10 comprising the invention is generally utilized by placing helmet 18 onto the head of a person using the invention, and positioning helmet 18 such that ear covers 22a, 22b are generally adjacent to and cover the wearer's ears, and so that apertures 14a, 14b of first and second sound gathering horns 12a, 12b and apertures 24a, 24b in ear covers are facing in a rearward direction or behind the wearer. Sounds from behind the wearer of the invention, such as the sounds associated with an approaching motor vehicle, are received in apertures 14a, 14b and then reflected or channelled through sound channelling tubes 16a, 16b to ear covers 22a, 22b respectively, wherein the channelled and amplified sound is introduced or communicated into the ears of a wearer via the apertures 26a, 26b in ends 28a, 28b of sound channelling tubes 16a, 16b. The tapered shape of sound channelling tubes 16a, 16b, which generally taper down from a larger diameter adjacent apertures 14a, 14b to a smaller diameter adjacent ear covers 22a, 22b, provide for passive amplification of the received sound. Ear covers 22a, 22b additionally eliminate wind noise, as related above, to facilitate hearing by the wearer of sounds directed through sound channelling tubes 16a, 16b. The rearward facing apertures 24a, 24b in ear covers 22a, 22b provide for additional rearward sound gathering.

Figure 5:
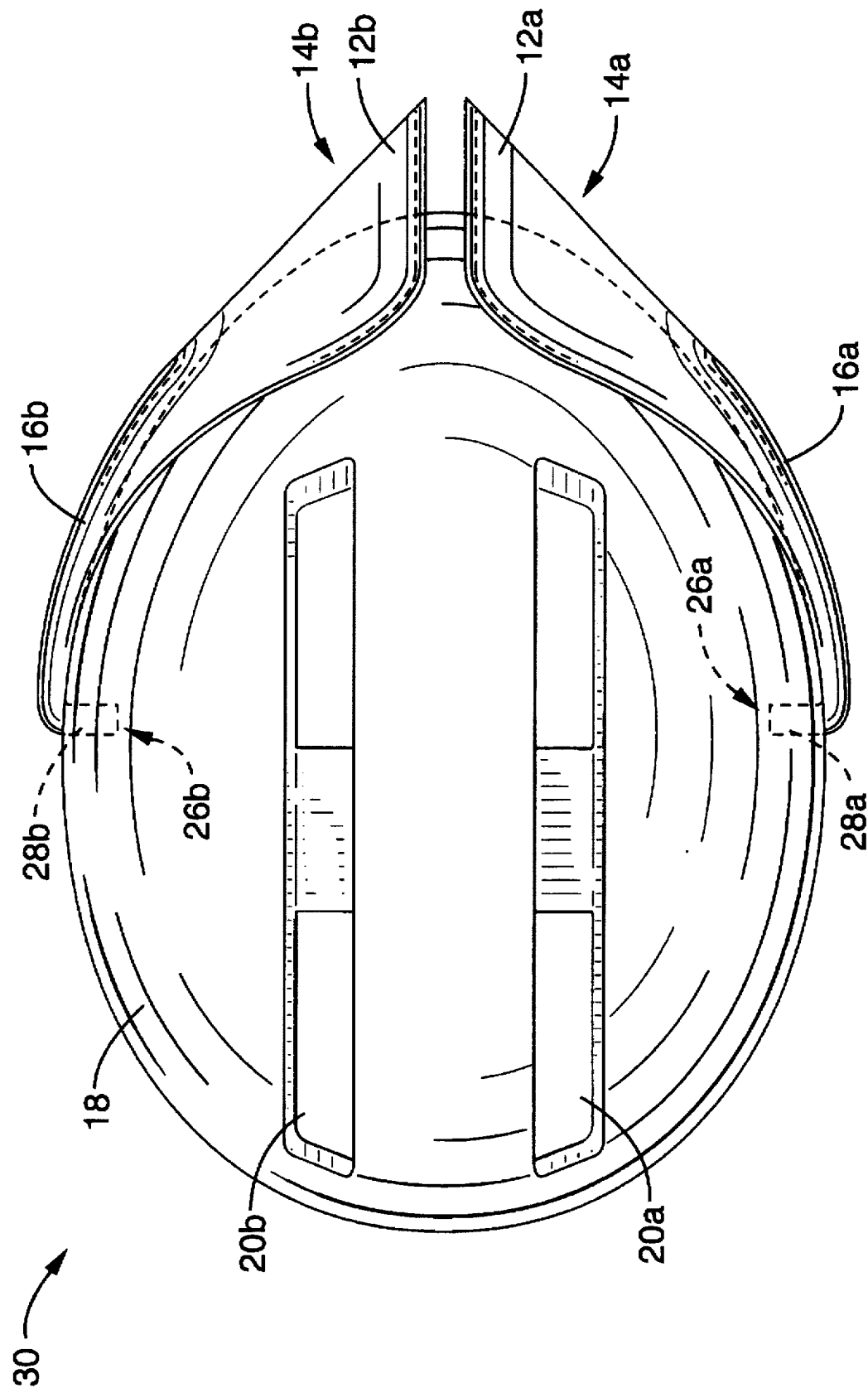
FIG. 5 is a top plan view of a second embodiment of a sound gathering apparatus in accordance with the present invention.
Figure 6:
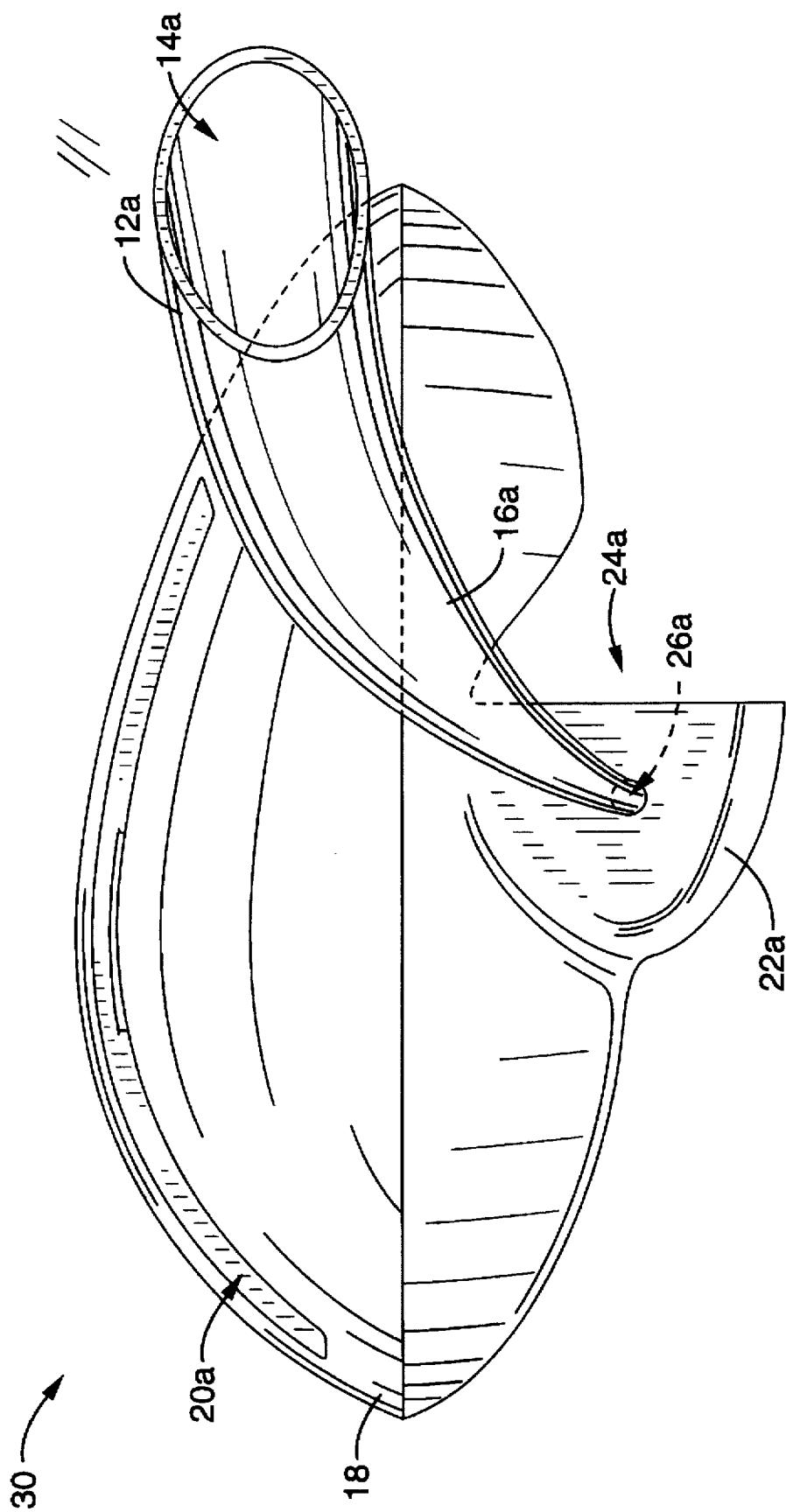
FIG. 6 is a side elevation view of the sound gathering apparatus of FIG. 5.

Referring now to FIG. 5 and FIG. 6, there is shown a second embodiment 30 of the invention, wherein like reference numerals denote like parts. In the sound gathering apparatus 30, sound gathering horns 12a, 12b are structured and configured such that apertures 14a, 14b point generally outward as well as rearward, to provide a greater angle of arc over which sound is received. As shown, apertures 14a, 14b are angularly offset outward at about forty-five degrees relative to the longitudinal axis of helmet 18. In the sound gathering apparatus 10 described above, apertures 14a, 14b face in a relatively straight rearward direction, and are generally normal to or at a right angle to the longitudinal axis of helmet 18. In all other respects, the sound gathering apparatus 30 is generally identical to the apparatus 10 described above.

Figure 7:
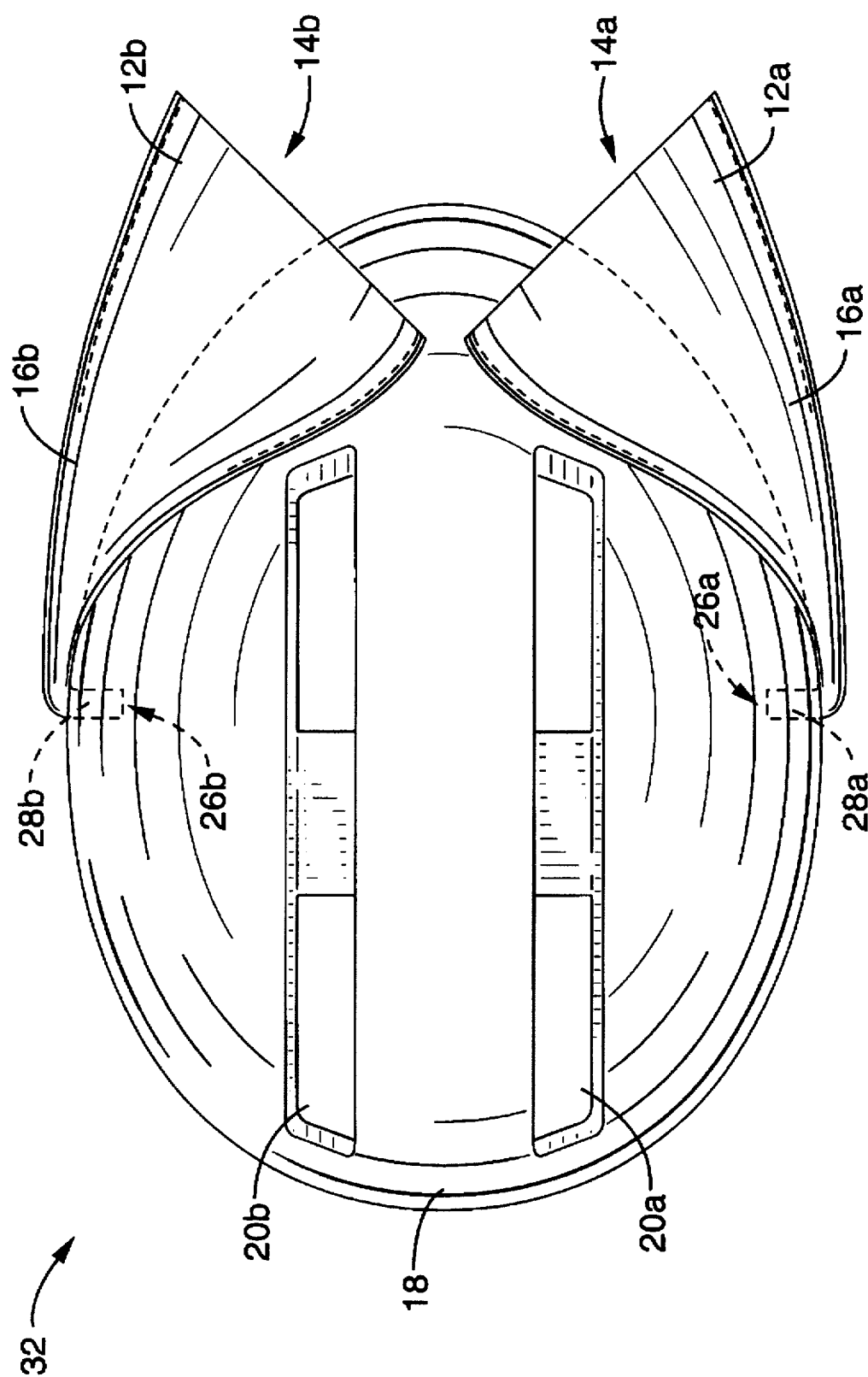
FIG. 7 is a top plan view of a third embodiment of a sound gathering apparatus in accordance with the present invention.

Referring next to FIG. 7, there is shown a third embodiment 32 of the invention, wherein like reference numerals denote like parts. In the apparatus 32, apertures 14a, 14b of sound gathering horns 12a, 12b are angled generally inward as well as rearward, to provide for sound gathering over a relatively narrow angle of arc. As shown, apertures 14a, 14b are angularly offset inward at an angle of about forty-five degrees relative to the longitudinal axis of helmet 18. In all other respects, the sound gathering apparatus 32 is generally identical to the apparatus 10 described above.

Figure 8:
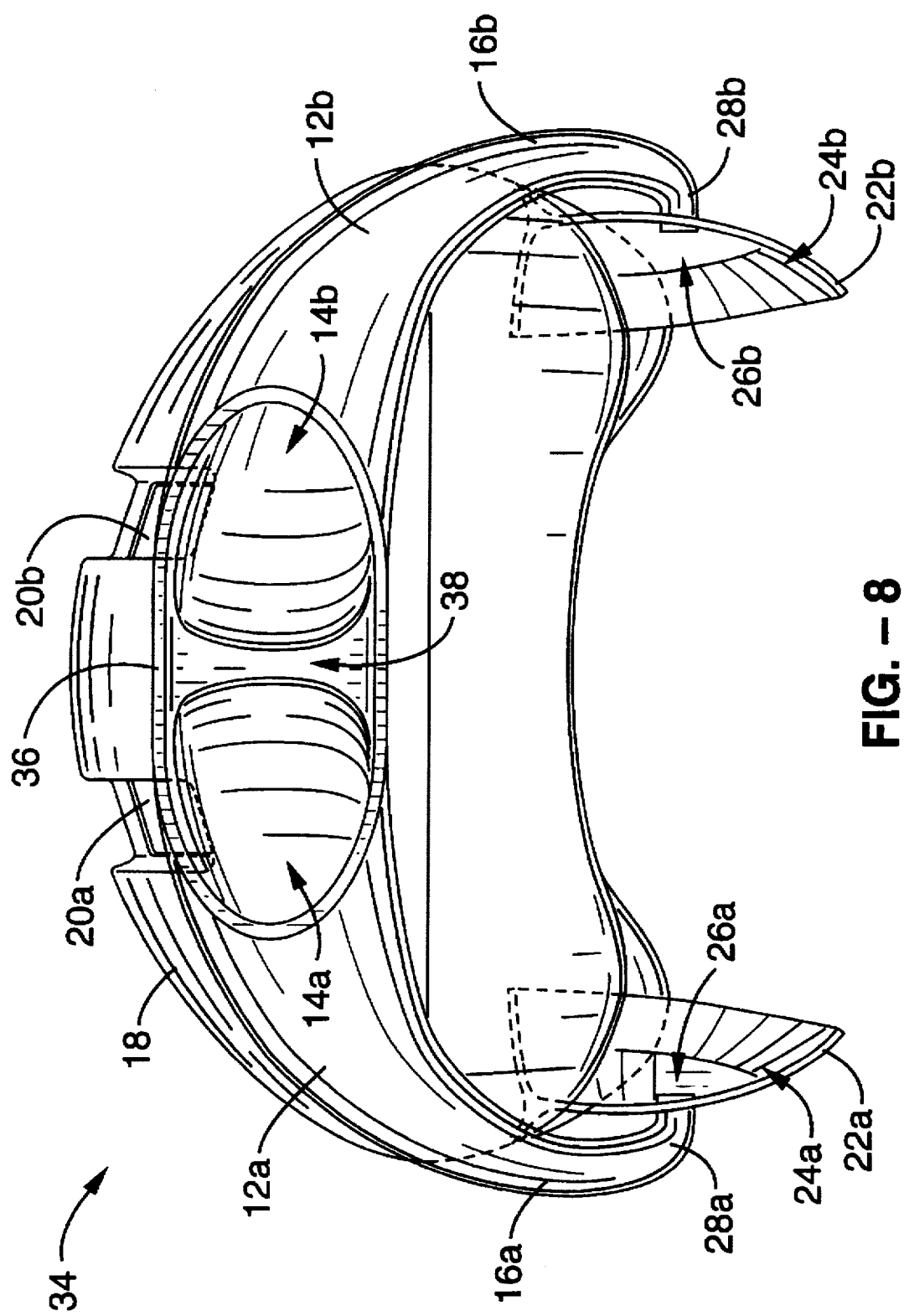
FIG. 8 is a rear view of a fourth embodiment of a sound gathering apparatus in accordance with the present invention.

Referring now to FIG. 8, there is shown a fourth embodiment of a sound gathering apparatus 34 in accordance with the invention, wherein like reference numerals denote like parts. The sound gathering apparatus 34 includes a sound gathering receptacle 36 having a single rearward facing aperture 38. Two sound horns 12, 12b are joined to sound gathering receptacle 36 so that their apertures 14a, 14b receive sound from a common source. In other works, sound gathering receptacle 36 bifurcates into sound gathering horns 12a, 12b. Sound received by receptacle 36 is directed and amplified via sound gathering tubes 16a, 16b to ear covers 22a, 22b as described above. Sound gathering receptacle 36 may be varied in shape according to sound gathering objectives, and may be structured and configured to gather sound over a narrow or wide angle of arc as required.

In the sound gathering apparatus 34, the pair of sound gathering receptacles as disclosed in the above embodiments have been generally joined together to form a single sound gathering receptacle 36 and generally share a common aperture 38. Alternatively, the apparatus 34 may be considered as comprising of two sound gathering receptacles which share a single aperture. In all other respects, however, the sound gathering apparatus 34 is the same as the embodiments related above and is used in generally the same manner.

Accordingly, it will be seen that the present invention provides a head-worn passive sound gathering apparatus for use by cyclists and the like which reduces or eliminates ambient wind noise due to air rushing past the cyclist's ears, and which receives sound from the rear direction and introduces the sound to the ears of the wearer of the invention. Although the description above contains many specificities, these should not be construed as limiting the scope of the invention but as merely providing illustrations of some of the presently preferred embodiments of this invention. Thus, the scope of the invention should be determined by the appended claims and their legal equivalents.

What is claimed is:

1. A passive sound gathering helmet apparatus, comprising:
    (a) a first sound gathering horn, said first sound gathering horn having a first aperture;
    (b) a first ear cover, said first ear cover acoustically coupled to said first sound gathering horn whereby sound waves entering said first sound gathering horn are transmitted to said first ear cover;
    (c) a second sound gathering horn, said second sound gathering horn having a second aperture;
    (d) a second ear cover, said second ear cover acoustically coupled to said second sound gathering horn whereby sound waves entering said second sound gathering horn are transmitted to said second ear cover;
    (e) a sound gathering receptacle, said sound gathering receptacle acoustically coupled to said first and second apertures of said first and second sound gathering horns; and
    (f) a helmet coupled to said first and second sound gathering horns, said first and second ear covers, and said sound gathering receptacle.

2. An apparatus as recited in claim 1, wherein said sound gathering horns are tapered in shape.

3. A head worn sound gathering helmet apparatus, comprising:
    (a) first and second sound gathering horns, each said sound gathering horn having an aperture, each said sound gathering horn having a sound channeling tube connected to each said aperture whereby sound waves received through each said aperture are transmitted through each said sound channeling tube;
    (b) first and second ear covers, said sound channeling tube of said first sound gathering horn acoustically coupled to said first ear cover, said sound channeling tube of said second sound gathering horn acoustically coupled to said second ear cover;
    (c) a sound gathering receptacle acoustically coupled to said apertures of said first and second sound gathering horns; and
    (d) a helmet coupled to said first and second sound gathering horns, said first and second ear covers, and said sound gathering receptacle.

4. An apparatus as recited in claim 3, wherein said helmet has a front and a rear and wherein said apertures in said first and second sound gathering horns are positioned in a substantially rearward facing orientation relative to said rear of said helmet.

5. An apparatus as recited in claim 3, wherein said first and second sound gathering horns are tapered in shape.

6. A head worn sound gathering helmet apparatus, comprising:
    (a) a helmet, said helmet having a first side and a second side, said helmet having a front and a rear;
    (b) a first sound gathering horn, said first sound gathering horn coupled to said helmet, said first sound gathering horn including a rearward facing aperture relative to said rear of said helmet;
    (c) a second sound gathering horn, said second sound gathering horn coupled to said helmet, said second sound gathering horn including a rearward facing aperture relative to said rear of said helmet;
    (d) a first ear cover, said first ear cover coupled to said first side of said helmet, said first ear cover acoustically coupled to said first sound gathering horn;

(e) a second ear cover, said second ear cover coupled to said second side of said helmet, said second ear cover acoustically coupled to said second sound gathering horn; and (f) a sound gathering receptacle acoustically coupled to said apertures of said first and second sound gathering horns.

7. An apparatus as recited in claim 6, wherein said first and second sound gathering horns are tapered in shape.

8. An apparatus as recited in claim 6, wherein said first sound gathering horn includes a first sound channelling tube portion, said first sound channelling tube portion communicating with said first ear cover, and wherein said second sound gathering horn includes a second sound channelling tube portion, said second sound channelling tube portion communicating with said second ear cover.

* * * * *